(12) United States Patent
Maruyama et al.

(10) Patent No.: US 11,090,295 B2
(45) Date of Patent: Aug. 17, 2021

(54) HYPROMELLOSE ACETATE SUCCINATE FOR USE AS HOT-MELT EXTRUSION CARRIER, HOT-MELT EXTRUSION COMPOSITION, AND METHOD FOR PRODUCING HOT-MELT EXTRUDATE

(71) Applicant: Shin-Etsu Chemical Co., Ltd., Tokyo (JP)

(72) Inventors: Naosuke Maruyama, Joetsu (JP); Shogo Warashina, Joetsu (JP); Fumie Kusaki, Joetsu (JP); Sakae Obara, Joetsu (JP); Kazuki Kikuchi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 215 days.

(21) Appl. No.: 14/453,935

(22) Filed: Aug. 7, 2014

(65) Prior Publication Data

US 2015/0044289 A1 Feb. 12, 2015

(30) Foreign Application Priority Data

Aug. 12, 2013 (JP) .............................. JP2013-167572

(51) Int. Cl.
| | |
|---|---|
| *A61K 31/4422* | (2006.01) |
| *A61K 9/14* | (2006.01) |
| *A61K 47/38* | (2006.01) |
| *A61K 9/20* | (2006.01) |

(52) U.S. Cl.
CPC .......... *A61K 31/4422* (2013.01); *A61K 9/146* (2013.01); *A61K 9/20* (2013.01); *A61K 47/38* (2013.01); *Y10T 428/2982* (2015.01)

(58) Field of Classification Search
CPC ...... A61K 31/4422; A61K 9/20; A61K 47/38; A61K 9/146; Y10T 428/2982
See application file for complete search history.

(56) References Cited

U.S. PATENT DOCUMENTS

| | | | |
|---|---|---|---|
| 4,226,981 | A | 10/1980 | Onda et al. |
| 4,983,593 | A | 1/1991 | Miyajima et al. |
| 5,456,923 | A | 10/1995 | Nakamichi et al. |
| 6,881,745 | B2 | 4/2005 | Hayes et al. |
| 2008/0260657 | A1 | 10/2008 | Butler et al. |
| 2009/0269403 | A1 | 10/2009 | Shaked et al. |
| 2011/0034478 | A1 | 2/2011 | Fang et al. |
| 2011/0123627 | A1 | 5/2011 | Fang et al. |
| 2011/0229570 | A1 | 9/2011 | Sugimoto et al. |

FOREIGN PATENT DOCUMENTS

| | | |
|---|---|---|
| EP | 2368544 | 9/2011 |
| EP | 2647648 | 10/2013 |
| JP | 04-290817 | 10/1992 |
| JP | 4290817 | 7/2009 |
| WO | WO 03/077827 A1 | 9/2003 |
| WO | WO 2008/138755 A2 | 11/2008 |
| WO | 2009129300 | 10/2009 |
| WO | 2009132208 | 10/2009 |
| WO | WO 2010/114928 A2 | 10/2010 |
| WO | 2012074042 | 6/2012 |
| WO | 2012122279 | 9/2012 |
| WO | 2012138529 | 10/2012 |
| WO | 2012152440 | 11/2012 |

OTHER PUBLICATIONS

European Search Report corresponding to European Application No. 14178879.4 dated Dec. 5, 2014.
First Office Action corresponding to Chinese Application No. 201410389913.7 dated May 18, 2016.
Additional Information submitted to the European Patent Office for opposition proceedings corresponding to European Application No. 14178879.4/Patent No. 2837391 (4 pages) (Jun. 15, 2018).
Additional Information submitted to the European Patent Office for opposition proceedings corresponding to European Application No. 14178879.4/Patent No. 2837391 (10 pages) (Feb. 25, 2019).
Additional Information submitted to the European Patent Office for opposition proceedings corresponding to European Application No. 14178879.4/Patent No. 2837391 (6 pages) (Apr. 29, 2019).
Application Studies of L-HPC and HPMCAS for Pharmaceutical Dosage Forms—Update—Presentation by Sakae OBARA Specialty Chemicals Research Center Shin-Etsu Chemical Co., Ltd. Niigata, Japan at ExcipientFest Americas 2012, San Juan, PR (Apr. 24-25, 2012).
Chung, Chan I. "Extrusion of Polymers: Theory & Practice" 2nd Edition, Chapter 2 (pp. 13-57) (2010).
Crowley et al. "Pharmaceutical Applications of Hot-Melt Extrusion: Part I" Drug Development and Industrial Pharmacy, 33:909-926 (2007).
English Translation of JP4290817, provided by Thomson Reuter (16 pages).
European Patent Office Communication of a Notice of Opposition corresponding to European Application No. 14178879.4/Patent No. 2837391 (1 page) (mailed Feb. 13, 2018).
European Patent Office Communication of a Notice of Opposition corresponding to European Application No. 14178879.4/Patent No. 2837391 (1 page) (mailed Feb. 20, 2018).

(Continued)

*Primary Examiner* — Hasan S Ahmed
(74) *Attorney, Agent, or Firm* — Myers Bigel, P.A.

(57) ABSTRACT

Provided are hypromellose acetate succinates (HPMCAS) for use as a hot-melt extrusion carrier having a volume average particle size ($D_{50}$) of from 70 to 300 as measured by dry laser diffraction and a loose bulk density of from 0.25 to 0.40 $g/cm^3$; and a hot-melt extrusion composition comprising the HPMCAS and a drug. Also provided is a method for producing a hot-melt extrudate including the steps of: hot-melting the hot-melt extrusion composition at a hot-melt temperature equal to or higher than a melting temperature of the HPMCAS, or at a hot-melt temperature equal to or higher than a temperature at which both of the HPMCAS and the drug become melt; and extruding the hot-melted composition.

12 Claims, No Drawings

(56) References Cited

OTHER PUBLICATIONS

Gogos et al. "Melting and Twin Screw Extrusion Laminar Dispersive and Distributive Mixing with Dissolution and Applications to Hot Melt Extrusion" In Proceedings of the 2nd Electron. Conf. Pharm. Sci., 1-31 (May 2012) available at https://sciforum.net/manuscripts/794/manuscript.pdf.
Horiba Scientific "A Guidebook to Particle Size Analysis" 33 pages (2016).
"Hot-Melt Extrusion with BASF Pharma Polymers" Extrusion Compendium, 2nd Revised and Enlarged Edition (Oct. 2012).
"Hypromellose Acetate Succinate" Handbook of Pharmaceutical Excipients, Sixth edition, pp. 330-332 (2009).
Kehlenbeck et al. "Possibilities to improve the short-term dosing constancy of volumetric feeders" Powder Technology, 138:51-56 (2003).
Liu et al. "Effects of extrusion process parameters on the dissolution behavior of indomethacin in Eudragit E PO solid dispersions" International Journal of Pharmaceutics, 383:161-169 (2010).
Luker, Keith "Single-screw Extrusion: Principles" Hot-melt Extrusion: Pharmaceutical Applications (14 pages) (2012).
Notice of Opposition corresponding to European Patent No. EP 2 837 391 (17 pages) (Feb. 5, 2018).
Notice of Opposition corresponding to European Patent No. EP 2 837 391 (10 pages) (Feb. 12, 2018).
"Pharmaceutical Extrusion Technology" (ed. I. Ghebre-Selassie et al.) (pp. 154, 185-186) (2003).
"Pharmaceutical Preformulation and Formulation: A Practical Guide from Candidate Drug Selection to Commercial Dosage Form" (ed. Mark Gibson) Chapter 11: Oral Solid Dosage Forms, p. 383 (2004).
Pictures from the web showing different hopper designs with links: https://www.gericke.net/fileadmin/user_upload/PDFs/Prospekte_Brochures/Englisch/646-2_UK_Gericke_Gravimetric_Feeding.pdf (2017); https://www.coperion.com/en/products-services/process-equipment/feeders (2019).
Prescott et al. "On Powder Flowability" Pharmaceutical Technology, pp. 60-84 and 326 (2000).
Printout from the website http://www.three-tec.ch/trichterbauformen.htm (1 page) (2017).
Schematic representation of a single-screw feeder taken from the website www.directindustry.com (2019).
"Shin-Etsu AQOAT, Hypromellose Acetate Succinate" Technical Brochure (20 pages) (2005).
"Size Reduction Systems" Fitz Mill Brochure (13 pages) (Dec. 2011).
U.S. Pharmacopeia definition of drug powder fineness according to General Chapter 81, US Pharmacopeia 29 (1 page) (2006).
World Health Organization "S.3.6. Bulk Density and Tapped Density of Powders" Final text for addition to the International Pharmacopoeia (6 pages) (Mar. 2012).
Zhou et al. "Understanding Material Properties in Pharmaceutical Product Development and Manufacturing: Powder Flow and Mechanical Properties" Journal of Validation Technology (pp. 65-77) (2010).
Examination Report corresponding to Indian Patent Application No. 2197/DEL/2014 (6 pages) (dated Mar. 27, 2019).
Representation for Opposition to Grant of Patent (Form 7A) corresponding to Indian Patent Application No. 2197/DEL/2014 (24 pages) (dated Sep. 30, 2018).
"Shin-Etsu AQOAT, Hypromellose Acetate Succinate" Technical Brochure (20 pages) (2009).

US 11,090,295 B2

HYPROMELLOSE ACETATE SUCCINATE FOR USE AS HOT-MELT EXTRUSION CARRIER, HOT-MELT EXTRUSION COMPOSITION, AND METHOD FOR PRODUCING HOT-MELT EXTRUDATE

RELATED APPLICATION

This application claims priority from Japanese Patent Application No. 2013-167572, filed Aug. 12, 2013, the disclosure of which is incorporated by reference herein in its entirety.

FIELD AND BACKGROUND OF THE INVENTION

The present invention relates to hypromellose acetate succinate (HPMCAS), a hot-melt extrusion composition comprising the HPMCAS, and a method for producing a hot-melt extrudate.

A method for producing a preparation by melt-extruding a mixture of a drug and a polymer under heating has recently attracted attentions.

For example, a solid dispersion obtained by solidifying a poorly water-soluble drug and a polymer through a hot-melt extrusion exhibits improved biodegradability since the drug is, in an amorphous form, molecularly dispersed in the polymer carrier and apparent solubility of the drug is markedly improved. The hot-melt extrusion can be carried out without a solvent so that it can be applied to water-labile drugs. In the absence of solvent recovery, the hot-melt extrusion provides various advantages including the advantages that concerns about safety or environment can be reduced, energy in a solvent recovery step can be saved, and the safety of workers can be improved. Further, different from a conventional batch production system, the hot-melt extrusion permits continuous production so that it has drawn attentions also from the standpoint of hourly productivity and consumption energy.

Examples of the polymer to be used for the hot-melt extrusion include hypromellose acetate succinate (hereinafter also called "HPMCAS") having four substituents in total introduced, more specifically, having two substituents, a methoxy group (—$OCH_3$) and a hydroxypropoxy group (—$OC_3H_6OH$) introduced into a cellulose skeleton to form ether structures and having two substituents, an acetyl group (—$COCH_3$) and a succinyl group (—$COC_2H_4COOH$) introduced to form ester structures.

With regard to an HPMCAS-containing solid dispersion obtained by the hot-melt extrusion method, there is, for example, proposed a method for producing a solid dispersion containing HPMCAS (commercially available "AS-LF" having a molar substitution of from 0.16 to 0.35 and an average particle size of 5 μm) and a poorly water-soluble drug through a hot-melt extrusion method in which water is added to the solid dispersion to reduce the glass transition temperature or softening temperature of the HPMCAS or the drug (WO 2003/077827).

There is also proposed a method for producing a preparation comprising posaconazole, which is a poorly water-soluble drug, and a hydroxypropylmethyl cellulose derivative polymer having a particle size of from 0.2 to 1 μm through hot-melt extrusion in which the hydroxypropylmethyl cellulose derivative polymer is HPMCAS (commercially available "AS-MF" having a molar substitution of from 0.15 to 0.34 and an average particle size of 5 μm, or "AS-MG" having a molar substitution of from 0.15 to 0.34 and an average particle size of 1 mm) (JP 2011-516612T, which is a Japanese phase publication of WO 2009/129300).

There is further proposed an enteric preparation in which a meltable substance such as hydrogenated castor oil is used as a binder and a core substance containing a pharmaceutical compound is coated with a film of an enteric substance having an average particle size of from 1 to 500 μm (JP04-290817A).

SUMMARY OF THE INVENTION

Commercially available HPMCAS having an average particle size of not more than 10 μm described in WO 2003/077827 or JP 2011-516612T, however, has low flowability of powder owing to a small particle size and a high agglomeration property. When a hot-melt extrudate is formed using a hot-melt extruder, a powder mixture of a drug and the above-mentioned HPMCAS is likely to form a bridge in the hopper of a feeder, thereby preventing constant feed and continuous operation. This results in reduction in uniformity of drug content and reduction in a weight ratio of the HPMCAS to the drug. The reason why the HPMCAS having such a small average particle size has inevitably been used conventionally is that the HPMCAS is mainly used as an enteric coating agent and the HPMCAS in a finer powder form has been demanded in order to form a uniform film with a water-dispersible enteric coating agent. Commercially available HPMCAS having an average particle size of from 0.5 to 1.0 mm to be used for solvent coating is excellent in powder flowability. However, when it is used for production of a solid dispersion with a hot-melt extruder, poor miscibility of the HPMCAS with a drug deteriorates the uniformity of the drug content in the resulting solid dispersion. The HPMCAS having a large average particle size has inevitably been used for solvent coating conventionally since a powder causing less dusting and easy to handle during preparation of a solution has been demanded.

JP 04-290817A relates to a dry coating composition comprising HPMCAS for coating the periphery of a core substance containing a pharmaceutical compound. Accordingly, the drug is not molecularly dispersed in an amorphous form in an enteric substance.

With the foregoing in view, the invention has been made. An object of the invention is to provide a hot-melt extrudate excellent in uniform miscibility between HPMCAS and a drug, and a method for producing the hot-melt extrudate in which a powder can be fed smoothly for hot-melt extrusion, by using a hot-melt extrusion composition comprising a HPMCAS having an average particle size within a predetermined range.

With a view to achieving the above-mentioned object, the present inventors have carried out an intensive investigation. As a result, it has been found that by adjusting the average particle size of HPMCAS to fall within a predetermined range, the resulting HPMCAS can be fed smoothly, and a hot-melt extrudate having high uniformity of miscibility between the HPMCAS and a drug can be produced, leading to the completion of the invention.

In one aspect of the invention, there is provided hypromellose acetate succinate for use as a hot-melt extrusion carrier having a volume average particle size ($D_{50}$) as measured by dry laser diffraction of from 70 to 300 μm and a loose bulk density of from 0.25 to 0.40 $g/cm^3$. In another aspect of the invention, there is also provided a hot-melt extrusion composition comprising the hypromellose acetate succinate and a drug. In a further aspect of the invention, there is also provided a method for producing a hot-melt extrudate comprising the steps of: hot-melting a hot-melt extrusion composition comprising hypromellose acetate succinate having a volume average particle size ($D_{50}$) as measured by dry laser diffraction of from 70 to 300 μm and having a loose bulk density of from 0.25 to 0.40 g/cm$^3$ and a drug at a hot-melt temperature equal to or higher than a melting temperature of the hypromellose acetate succinate, or at a hot-melt temperature equal to or higher than a temperature at which both the hypromellose acetate succinate and the drug become melt; and extruding the hot-melted composition.

According to the invention, powder feeding in hot-melt extrusion can be carried out more smoothly than ever before, and owing to the improved miscibility with a drug, a hot-melt extrudate having a uniform drug content can be produced continuously.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

HPMCAS has a volume-average particle size ($D_{50}$) of from 70 to 300 μm, preferably from 100 to 280 μm, more preferably from 100 to 200 μm. The volume-average particle size ($D_{50}$) is measured by using dry laser diffraction. When HPMCAS has a volume-average particle size of less than 70 μm, it has low powder flowability so that it forms a bridge in the hopper of a feeder, thereby preventing the continuous operation. In addition, owing to deteriorated miscibility with a drug and deteriorated uniformity of drug content, the resulting solid preparation cannot have therein a necessary amount of the drug. Further, owing to a decrease in the weight ratio of the HPMCAS to the drug, the drug does not become amorphous, thereby reducing the improvement of drug solubility. When HPMCAS has a volume-average particle size of more than 300 μm, a difference in the average particle size from the drug typically having an average particle size of from 1 to 50 μm, becomes too large, so that segregation occurs in the hopper and the drug content varies. As a result, owing to deterioration in uniformity of drug content, the resulting solid preparation cannot have therein a necessary amount of the drug. When the particle size of HPMCAS is too large during hot-melting, the HPMCAS cannot be melted sufficiently, thereby reducing improvement of drug solubility.

The term "dry laser diffraction" means a method comprising the steps of subjecting a powder sample blown by means of compressed air to a laser beam, and measuring a diffraction intensity thereof to determine a volume-average particle size. For example, the method utilizes "Mastersizer" produced by Malvern Instruments, UK, or "HELOS" produced by Sympatec, Germany. According to description of, for example, "Kaitei Zoho Funtai Bussei Zusetsu" ("revised and enlarged edition of Illustration of Powder Physical Properties") edited by The Society of Powder Technology, Japan and The Association of Powder Method Industry and Engineering, Japan, published by Nikkei Gijutsu Tosho, 1985, p 88, the volume-average particle size is calculated based on the equation; $\{\Sigma(nD^3)/\Sigma n\}^{1/3}$ wherein D is a particle diameter, n is the number of particles having said particle diameter, and Σn is a total number of particles. $D_{50}$ means a particle size at 50% in the cumulative particle size distribution.

The loose bulk density of the HPMCAS is from 0.25 to 0.40 g/ml, preferably from 0.30 to 0.40 g/ml, more preferably from 0.33 to 0.38 g/ml. When HPMCAS has a loose bulk density of less than 0.25 g/ml, the HPMCAS becomes too light so that it forms a bridge in the hopper of a feeder, thereby preventing the continuous operation. In addition, owing to deterioration in miscibility with a drug and deterioration in uniformity of drug content, the resulting solid preparation cannot have therein a necessary amount of the drug, and owing to a decrease in a weight ratio of the HPMCAS to the drug, the drug does not become amorphous, thereby reducing the improvement of drug solubility. When HPMCAS has a loose bulk density of more than 0.40 g/ml, the HPMCAS becomes too heavy so that it causes segregation in the hopper and variation in drug content. In addition, the HPMCAS having an excessively high loose bulk density requires much time for hot-melting the HPMCAS, leading to insufficient melting of the HPMCAS and reduction of improvement of drug solubility.

The term "loose bulk density" means a bulk density in a loosely filled state and the loose bulk density can be determined in the method comprising the steps of: uniformly feeding a sample into a cylindrical vessel (made of stainless) having a diameter of 5.03 cm, a height of 5.03 cm and a volume of 100 ml through a Japan Industrial Standards (JIS) 22-mesh sieve having openings of 710 μm from 23 cm above the vessel; leveling off the top surface of the sample; and weighing the vessel filled with the sample.

The degree of compaction of the HPMCAS is preferably from 15 to 40%, more preferably from 20 to 35% from the standpoint of flowability.

The term "degree of compaction" means a bulk-decreasing degree and can be calculated from the following equation:

$$\text{Degree of compaction (\%)} = [\{(\text{tapped bulk density}) - (\text{loose bulk density})\}/(\text{tapped bulk density})] \times 100$$

Herein, the term "tapped bulk density" means the bulk density measured after the sample is densely filled by tapping. The term "tapping" means an operation of dropping a vessel filled with a sample from a predetermined height in repetition to give a light impact onto the bottom of the vessel, thereby filling the vessel with the sample densely. In practice, after the loose bulk density is measured by leveling off the top surface of the sample and then weighing the vessel filled with the sample, a cap is put on the vessel. The sample powder is added thereto until it reaches the upper end of the cap, and then tapped 180 times from a tapping height of 1.8 cm. After completion of the tapping, the cap is removed and the top surface of the powder is leveled at the upper surface of the vessel. The bulk density in this state is designated as "tapped bulk density". The above-described measurement operation can be carried out using a powder tester "PT-S", produced by Hosokawa Micron Corporation.

The angle of repose of the HPMCAS is preferably from 30 to 45°, more preferably from 30 to 40° from the standpoint of flowability. The angle of repose can be determined by using a powder tester "PT-S" produced by Hosokawa Micron Corporation, allowing a sample powder to flow down from a height of 75 mm onto a disc-shaped stage being made of a metal and having a diameter of 80 mm until it makes a constant angle, and measuring an angle between the accumulated powder and the stage. The smaller the angle becomes, the more excellent flowability the powder has.

The molar substitution degree of methoxy groups, which are substituents of the HPMCAS, is not particularly limited, but is preferably from 0.70 to 2.90, more preferably from 1.00 to 2.40, still more preferably from 1.4 to 1.9.

The molar substitution degree of hydroxypropoxy groups, which are substituents of the HPMCAS, is not particularly limited, but is preferably from 0.20 to 1.50, more preferably from 0.2 to 1.0, still more preferably from 0.40 to 0.90.

The molar substitution degree of acetyl groups, which are substituents of the HPMCAS, is not particularly limited, but is preferably from 0.10 to 2.50, more preferably from 0.10 to 1.00, still more preferably from 0.40 to 0.95.

The molar substitution degree of succinyl groups, which are substituents of the HPMCAS, is not particularly limited, but is preferably from 0.10 to 2.50, more preferably from 0.10 to 1.00, still more preferably from 0.10 to 0.60.

The contents of the substituents of the HPMCAS including the hydroxypropoxy group can be measured in accordance with the method described in "Hypromellose acetate succinate" of Official Monographs of the Japanese Pharmacopoeia, Sixteenth Edition, Supplement I.

The viscosity at 20° C. of a 2% by weight aqueous dilute sodium hydroxide (0.1 mol/L NaOH) solution of the HPMCAS is preferably from 1.1 to 20 mPa·s, more preferably from 1.5 to 3.6 mPa·s. When the viscosity is less than 1.1 mPa·s, a shear force may not be applied during hot-melt extrusion because of a too low melt viscosity, which may cause idle running of a piston or screw, or may cause difficulty in extruding from a discharge port. When the viscosity is more than 20 mPa·s, the hot-melt extrusion composition comprising the HPMCAS may have a too high viscosity and an excessive torque may be applied to a piston or screw, which may prevent rotation of the piston or screw, or may stop the machine for safety reasons. The viscosity can be measured in accordance with General Tests of HPMCAS in the Japanese Pharmacopoeia, Sixteenth Edition.

HPMCAS can be prepared using the method described in, for example, JP 54-061282A. Hypromellose also called "hydroxypropylmethyl cellulose" (hereinafter also called "HPMC") and used as a raw material is dissolved in glacial acetic acid, and subjected to addition of acetic anhydride and succinic anhydride as esterifying agents and addition of sodium acetate as a reaction catalyst. The resulting mixture is allowed to react under heating. After completion of the reaction, a large amount of water is added to the reaction mixture to allow HPMCAS to precipitate. The precipitate thus obtained is washed with water and then dried to obtain a granular dry product having a volume-average particle size of from about 0.5 to 2.0 mm.

The dry product thus obtained is ground in a grinder to obtain HPMCAS. Since the HPMCAS has a low softening temperature, an impact grinder having a structure not easily causing an increase in the temperature of the ground product such as a jet mill, a knife mill or a pin mill is preferred.

The drug is not particularly limited as long as it is orally administrable. Examples of the drug include drugs for the central nervous system; drugs for the cardiovascular system; drugs for the respiratory system; drugs for the digestive system; antibiotics; antitussives/expectorants; antihistamines; analgesics, antipyretics and anti-inflammatory drugs; diuretics; autonomic drugs; antimalarial drugs; antidiarrheal agents; psychotropic drugs; and drugs of vitamins and derivatives thereof.

Examples of the drugs for the central nervous system include diazepam; idebenone; aspirin; ibuprofen; paracetamol; naproxen; piroxicam; dichlofenac; indomethacin; sulindac; lorazepam; nitrazepam; phenytoin; acetaminophen; ethenzamide; ketoprofen; and chlordiazepoxide.

Examples of the drugs for the cardiovascular system include molsidomine; vinpocetine; propranolol; methyldopa; dipyridamol; furosemide; triamterene; nifedipine; atenolol; spironolactone; metoprolol; pindolol; captopril; isosorbide nitrate; delapril hydrochloride; meclofenoxate hydrochloride; diltiazem hydrochloride; etilefrine hydrochloride; digitoxin; propranolol hydrochloride; and alprenolol hydrochloride.

Examples of the drugs for the respiratory system include amlexanox; dextromethorphan; theophylline; pseudoephedrine; salbutamol; and guaiphenecin.

Examples of the drugs for the digestive system include benzimidazole-based drugs having anti-ulcer action such as 2-[(3-methyl-4-(2,2,2-trifluoroethoxy)-2-pyridyl)methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotics include talampicillin hydrochloride; bacampicillin hydrochloride; cephaclor; and erythromycin.

Examples of the antitussives/expectorants include noscapine hydrochloride; carbetapentane citrate; dextromethorphan hydrobromide; isoaminile citrate; and dimemorfan phosphate.

Examples of the antihistamines include chlorpheniramine maleate; diphenhydramine hydrochloride; and promethazine hydrochloride.

Examples of the analgesics, antipyretics and anti-inflammatory drugs include ibuprofen; diclofenac sodium; flufenamic acid; sulpyrine; aspirin; and ketoprofen.

Examples of the diuretics include caffeine.

Examples of the autonomic drugs include dihydrocodeine phosphate; dl-methylephedrine hydrochloride; atropine sulfate; acetylcholine chloride; and neostigmine.

Examples of the antimalarial drugs include quinine hydrochloride.

Examples of the antidiarrheal agents include loperamide hydrochloride.

Examples of the psychotropic drugs include chlorpromazine.

Examples of the drugs of vitamins and derivatives thereof include Vitamin A; Vitamin B1; fursultiamine; Vitamin B2; Vitamin B6; Vitamin B12; Vitamin C; Vitamin D; Vitamin E; Vitamin K; calcium pantothenate; and tranexamic acid.

According to the invention, in particular, use of the HPMCAS as a carrier for a poorly water-soluble drug can improve solubility of the poorly water-soluble drug. The term "poorly water-soluble drug" as used herein means a drug which is, in water, "slightly soluble", "very slightly soluble", or "practically insoluble, or insoluble" described in the Japanese Pharmacopoeia, Sixteenth Edition. When 1 g or 1 mL of a drug in solid form is put in a beaker, the water is poured in the beaker, and the resulting mixture is vigorously shaken for mixing for 30 seconds at 5-minute intervals at 20±5° C., the term "slightly soluble" means the degree of dissolution in which water of from 100 mL to less than 1000 mL is required to dissolve the drug within 30 minutes. The term "very slightly soluble" means the degree of dissolution in which water of from 1000 mL to less than 10000 mL is required to dissolve the drug within 30 minutes in the same manner. The term "practically insoluble, or insoluble" means the degree of dissolution in which water of 10000 mL and more is required to dissolve 1 g or 1 mL of a pharmaceutical in solid form within 30 minutes in the same manner.

In the above-mentioned pharmaceutical test, the dissolution of a poorly water-soluble drug means that it dissolves in water or becomes miscible with water, and as a result, fibers or the like are not present or if any, only a trace amount of them is present.

Specific examples of the poorly water-soluble drug include azole-based compounds such as itraconazole, ketoconazole, fluconazole, and metconazole; dihydropyridine-based compounds such as nifedipine, nitrendipine, amlodipine, nicardipine, nilvadipine, felodipine, and efonidipine; propionic acid-based compounds such as ibuprofen, ketoprofen, and naproxen; and indole-acetic acid-based compounds such as indomethacin and acemetacin; Additional examples include griseofulvin; phenytoin; carbamazepine; and dipypridamole.

A weight ratio of the HPMCAS to the drug is not particularly limited. It is preferably from 1:0.01 to 1:100, more preferably from 1:0.1 to 1:10, still more preferably from 1:0.2 to 1:5 from the standpoint of storage stability in amorphized form.

According to the invention, the composition may further comprise an optional additive such as a plasticizer or a surfactant in order to improve formability during hot-melt extrusion.

Examples of the plasticizer include acetone; higher alcohols including preferably $C_{10}$ to $C_{20}$ alcohols such as cetyl alcohol and stearyl alcohol; polyhydric alcohols including preferably diol, triol, tetraol, pentaol and hexaol such as mannitol, sorbitol and glycerin; beeswax; triethyl citrate; alkylene glycols such as polyethylene glycol and propylene glycol; triacetin; dibutyl sebacate; glycerin monostearate; and monoglycerin acetate.

Examples of the surfactant include anionic surfactants such as sodium lauryl sulfate; nonionic surfactants such as diglycerides, poloxamers, polyoxyethylene sorbitan fatty acid esters (Tween 20, 60, and 80), glycerin fatty acid esters, and propylene glycol fatty acid esters; and natural surfactants such as lecithin and sodium taurocholate.

The composition comprises the plasticizer in an amount of preferably 30% by weight or less, and the surfactant in an amount of preferably 10% by weight or less, each on basis of the weight of the HPMCAS from the standpoint of storage stability.

The hot-melt extrudate may optionally comprise various additives ordinarily used in this field such as an excipient, a binder, a disintegrant, a lubricant, and an agglomeration preventive, so that the hot-melt extrudate can be used as an oral solid preparation such as a tablet, a granule, a fine granule, a capsule and a film formulation.

Examples of the excipient include a sugar such as sucrose, lactose, mannitol and glucose; starch; and crystalline cellulose. The excipient may be comprised in an amount of from 5 to 80% by weight by the solid preparation.

Examples of the binder include polyvinyl alcohol; polyacrylic acid; polyvinylpyrrolidone; hydroxyethyl cellulose; hydroxypropylmethyl cellulose; hydroxypropyl cellulose; macrogols; gum Arabic; gelatin; and starch. The binder may be comprised in an amount of from 0.5 to 5% by weight by the solid preparation.

Examples of the disintegrant include low-substituted hydroxypropyl cellulose carmellose or salts thereof; croscarmellose sodium; carboxymethyl starch sodium; crospovidone; crystalline cellulose; and crystalline cellulose carmellose sodium. The disintegrant may be comprised in an amount of from 1 to 10% by weight by the solid preparation.

Examples of the lubricant and the agglomeration additive include talc; magnesium stearate; calcium stearate; colloidal silica; stearic acid; waxes; hydrogenated oil; polyethylene glycols; and sodium benzoate. The lubricant and/or the agglomeration additive may be comprised respectively in an amount of from 0.1 to 5% by weight by the solid preparation.

The oral solid preparation thus obtained may comprise film coating with a water-soluble coating agent such as methyl cellulose or hypromellose, or enteric coating with an enteric coating agent such as hypromellose acetate succinate, hypromellose phthalate or a methacrylate acrylate copolymer.

Next, a method for producing a hot-melt extrudate will be described.

First, a hot-melt extrusion composition is prepared by mixing HPMCAS having a volume-average particle size ($D_{50}$) of from 70 to 300 μm and a loose bulk density of from 0.25 to 0.40 g/cm$^3$, a drug and an optional component. The hot-melt extrusion composition thus obtained is charged in a hot-melt extruder from a hopper thereof and extruded into a desired shape such as columnar or film shape as well as round or quadrangular shape, to obtain a hot-melt extrudate.

The hot-melt extruder is not particularly limited as long as it has a structure capable of heating the HPMCAS, a drug and others in the system for melting; kneading the resulting mixture with application of a shear force with a piston or screw to the mixture; and then extruding the kneaded mixture from a die. In the standpoint of obtaining a more uniform extrudate, a twin-screw extruder is preferable. Specific examples include "Capilograph" (uniaxial piston extruder) produced by Toyo Seiki Seisaku-sho, "Nano-16" (twin-screw extruder) produced by Leistritz, and "MiniLab" (twin-screw extruder) and "PharmaLab" (twin-screw extruder) produced by Thermofisher Scientific.

The hot-melt temperature is not particularly limited. The hot-melt temperature is preferably a temperature at which the hot-melt extrusion composition is melted for smooth extrusion and degradation of the drug or polymer owing to heat can be avoided as much as possible. More specifically, when a solid dispersion is not formed, the hot-melt temperature is preferably a temperature equal to or higher than the melting temperature of the HPMCAS. When a solid dispersion is formed, the hot-melt temperature is preferably a temperature equal to or higher than the temperature at which both the HPMCAS and the drug become melt. Also when addition of the drug decreases the melting temperature of the HPMCAS, the hot-melt temperature is preferably equal to or higher than the temperature at which both the HPMCAS and the drug become melt. More specifically, the hot-melt temperature is preferably from 50 to 250° C., more preferably from 60 to 200° C., still more preferably from 90 to 190° C. When the hot-melt temperature is less than 50° C., extrusion may become difficult to be carried out owing to insufficient melting. When the hot-melt temperature is higher than 250° C., the molecular weight may be reduced owing to degradation of the HPMCAS or the drug, and deactivation may take place owing to hydrolysis of the substituents.

The hot-melt extrusion conditions are not particularly limited as long as they permit extrusion of a hot-melt extrusion composition having a viscosity of preferably from 1 to 100000 Pa·s during hot-melt extrusion. When a uniaxial piston extruder is used, an extrusion rate is preferably from 1 to 1000 mm/min, more preferably from 10 to 500 mm/min. When a twin-screw extruder is used, a screw rotation number is preferably 1 to 1000 rpm, more preferably 1 to 500 rpm. When the extrusion rate is less than 1 mm/min or the screw rotation number is less than 1 rpm, thermal degradation may occur owing to a long time of staying in the system. When the extrusion rate is more than 1000 mm/min or the screw rotation number is more than 1000 rpm, a hot-melt procedure at the kneading part may become insufficient so that a melt condition of the drug and the polymer in the hot-melt extrudate may not be uniform.

The hot-melt extrudate obtained by extrusion is cooled after a discharge port of the die by natural air of room temperature (from 1 to 30° C.) or by cooling air. In order to minimize the thermal degradation of a drug, and in order to prevent recrystallization of a drug if the drug is an amorphized drug, the hot-melt extrudate is cooled to preferably 50° C. or less, more preferably room temperature or lower (30° C. or less) is desired.

The hot-melt extrudate after cooling may be optionally pelletized into pellets of from 0.1 to 5 mm by using a cutter, or the pellets thus obtained may be ground into granules or powders as particle size control. For grinding, an impact grinder such as a jet mill, a knife mill or a pin mill is preferred because the structure of the impact grinder is not likely to cause a temperature increase of the ground product. When the temperature in the cutter or grinder becomes high, particles may adhere firmly to each other owing to thermal softening of the HPMCAS so that grinding under cooling air is preferred.

EXAMPLES

The invention will hereinafter be described specifically by Examples and Comparative Examples. However, it should not be construed that the invention is limited to or by Examples.

<Production of HPMCAS-7>

In a 50-L kneader, 12 kg of glacial acetic acid was placed, and 6 kg of hypromellose (HPMC) having a molar substitution degree of methoxy groups of 1.91 and a molar substitution degree of hydroxypropoxy groups of 0.24 was added into the kneader to dissolve the HPMC in the glacial acetic acid. To the resulting solution were added 3.5 kg of acetic anhydride, 1.2 kg of succinic anhydride and 2.9 kg of sodium acetate, and the resulting mixture was allowed to react at 85° C. for 5 hours. After purified water (6.7 kg) was added to the reaction mixture and the resulting mixture was stirred, purified water was further added thereto to allow a HPMCAS in granular form to precipitate. A crude HPMCAS was collected by filtration. The crude HPMCAS was washed with purified water, dried, and then sieved through 10-mesh sieve having openings of 1700 μm to obtain HPMCAS-7 having final water content of 1.2% by weight.

The content of each substituent of the resulting HPMCAS-7 was measured in accordance with the method described in the Japanese Pharmacopoeia, Sixteenth Edition, Supplement I. As a result, HPMCAS-7 was found to have methoxy content of 22.9% by weight (molar substitution degree of methoxy: 1.87), hydroxypropoxy content of 7.0% by weight (molar substitution degree of hydroxypropoxy: 0.24), acetyl content of 7.9% by weight (molar substitution degree of acetyl: 0.47), and succinyl content of 12.7% by weight (molar substitution degree of succninyl: 0.32).

HPMCAS-7 thus obtained had a volume-average particle size of 500 μm and a loose bulk density of 0.420.

<Production of HPMCAS-1>

HPMCAS-7 was ground using a pin mill "100UPZ" produced by Hosokawa Micron Corporation at a feed rate of 20 kg/hr and a disc rotational speed of 1500 rpm to obtain HPMCAS-1 having powder properties as shown in Table 1.

<Production of HPMCAS-2>

HPMCAS-7 was ground using a jet mill "CPY-2" produced by Nippon Pneumatic Mfg. Co., Ltd. at a feed rate of 20 kg/hr and a grinding pressure of 0.4 MPa to obtain HPMCAS-2 having powder properties as shown in Table 1.

<Production of HPMCAS-3>

HPMCAS-7 was ground using a pin mill "100UPZ" produced by Hosokawa Micron Corporation at a feed rate of 20 kg/hr and a disc rotational speed of 1000 rpm to obtain HPMCAS-3 having powder properties as shown in Table 1.

<Production of HPMCAS-4>

HPMCAS-7 was ground using a pin mill "100UPZ" produced by Hosokawa Micron Corporation at a feed rate of 20 kg/hr and a disc rotational speed of 500 rpm to obtain HPMCAS-4 having powder properties as shown in Table 1.

<Production of HPMCAS-6>

HPMCAS-7 was ground using a jet mill "CPY-2" produced by Nippon Pneumatic Mfg. Co., Ltd. at a feed rate of 10 kg/hr and a grinding pressure of 0.5 MPa to obtain HPMCAS-6 having powder properties as shown in Table 1.

<HPMCAS-5>

As HPMCAS-5, "Shin-Etsu AQOAT AS-MF" produced by Shin-Etsu Chemical Co., Ltd. having a volume-average particle size of about 5 μm was used as a commercially available fine power of HPMCAS.

<Evaluation of Flowability of HPMCAS-1 to 7>

Measurement results of a loose bulk density, a tapped bulk density, a degree of compaction, and an angle of repose of each of the thus-obtained HPMCAS powders by using a powder tester "PT-S" produced by Hosokawa Micron Corporation are shown in Table 1. With respect to the degree of compaction and the angle of repose serving as an indicator of flowability, HPMCAS-1 to 4 exhibit lower values than those of HPMCAS-5 and 6, which suggests that HPMCAS-1 to 4 are superior in flowability.

TABLE 1

| sample | volume-average particle size (μm) | loose bulk density (g/cm$^3$) | degree of compaction | angle of repose (°) |
| --- | --- | --- | --- | --- |
| HPMCAS-1 | 76 | 0.326 | 28.2 | 38.7 |
| HPMCAS-2 | 105 | 0.384 | 20.2 | 36.4 |
| HPMCAS-3 | 163 | 0.336 | 20.6 | 36.2 |
| HPMCAS-4 | 271 | 0.394 | 22.9 | 35.1 |
| HPMCAS-5 | 5 | 0.230 | 47.0 | 55.0 |
| HPMCAS-6 | 21 | 0.278 | 39.8 | 42.5 |
| HPMCAS-7 | 500 | 0.420 | 10.0 | 35.0 |

<Evaluation of Feed Rate of HPMCAS-1 to 7>

The 300 g of each of HPMCAS-1 to 7 was introduced into a powder feed port of a single screw powder feeder having a screw diameter of 55 mm and a rotational speed of screw of 10 rpm, and a powder feed rate (g/min) at a discharge port was measured six times at intervals of 20 seconds. The above-mentioned operation was conducted three times and a coefficient of variation Cv [Cv=(standard deviation/average)×100] serving as an indicator of variation in feed rate was determined from an average of the feed rates measured 18 times in total and a standard deviation. The results are shown in Table 2.

HPMCAS-1 to 4 having lower Cv values than those of HPMCAS-5 to 7 are superior in flowability and superior in constant feeding of powder during hot-melt extrusion.

TABLE 2

| sample | coefficient of variation Cv of feed rate of HPMCAS (%) |
| --- | --- |
| HPMCAS-1 | 4.2 |
| HPMCAS-2 | 3.8 |
| HPMCAS-3 | 4.3 |
| HPMCAS-4 | 4.1 |
| HPMCAS-5 | 12.0 |
| HPMCAS-6 | 8.0 |
| HPMCAS-7 | 6.5 |

<Evaluation of Uniform Miscibility of HPMCAS-1 to 7>

In a polyethylene bag were charged 30 g of vitamin C powder having an average particle size of 25 μm as a model drug and 90 g of each of HPMCAS-1 to 7. After shaken ten times with hands, the resulting mixture was placed in a powder feeder "Accurate" produced by KUMA Engineering Co., Ltd. and then discharged at a screw rotational speed of 80 rpm. From the HPMCAS thus discharged, about 4 g was sampled nine times as time elapsed. From each of the fractions, 0.4 g was precisely weigh and vitamin C was extracted using purified water. After filtration through a membrane filter and dilution, an absorbance was measured using a UV spectrophotometer at a wavelength of 257 nm and an optical path length of 10 mm. A coefficient of variation Cv, Cv=(standard deviation/average)×100, was determined from the vitamin C content in each of the fractions. The results are shown in Table 3. The values of the coefficient of variation for HPMCAS-1 to 4 are lower than those for HPMCAS-5 to 7, exhibiting that HPMCAS-1 to 4 are superior in miscibility during hot-melt extrusion.

TABLE 3

| sample | coefficient of variation Cv of vitamin C content (%) |
| --- | --- |
| HPMCAS-1 | 5.2 |
| HPMCAS-2 | 3.8 |
| HPMCAS-3 | 4.3 |
| HPMCAS-4 | 4.1 |
| HPMCAS-5 | 7.0 |
| HPMCAS-6 | 12.0 |
| HPMCAS-7 | 10.6 |

<Examples 1 to 4 and Comparative Examples 1 to 2>
Preparation of Solid Dispersion Hot-melt extrusion compositions were prepared by mixing each of HPMCAS-1 (Example 1), HPMCAS-2 (Example 2), HPMCAS-3 (Example 3), HPMCAS-4 (Example 4), HPMCAS-7 (Comparative Example 1) with nifedipine as a poorly water-soluble drug in a mortar (at a HPMCAS: nifedipine mass ratio of 1:0.5). Hot-melt extrusion at 160° C. of each of the resulting compositions was carried out using a hot-melt extrusion test apparatus "Capilograph" (uniaxial piston melt extruder) produced by Toyo Seiki Seisaku-sho, Ltd. having a die diameter of 1 mm and a die height of 10 mm at an extrusion rate of 50 mm/min.

The resulting hot-melt extrudate was ground using a grinder "Wonder Blender WB-1" produced by Osaka Chemical Co., Ltd. at 20000 rpm, followed by filtration through a 30-mesh sieve. The powder thus obtained were subjected to the dissolution test described in the Japanese Pharmacopoeia, Sixteenth Edition.

A dissolution ratio (% by weight) of nifedipine eluted from 270 mg of the resulting powder (corresponding to 90 mg of nifedipine) after 10 minutes was measured by using 900 ml of 2nd fluid having a pH value of 6.8 to be used in Disintegration Test of the Japanese Pharmacopoeia, Sixteenth Edition and a dissolution tester "NTR-6100A" produced by Toyama Sangyo Co., Ltd. at a paddle rotational speed of 100 rpm. The amount of nifedipine was determined from the UV absorbance at 325 nm with an optical path length of 10 mm based on an absorbance calibration curve drawn at known concentrations in advance. The results are shown in Table 4. In Comparative Example 2, the same test was conducted on nifedipine bulk powder. The dissolution ratio after 10 minutes was measured because a maximum dissolution ratio is usually observed after 10 minutes.

TABLE 4

| | sample | dissolution ratio of nifedipine after 10 min (% by weight) |
| --- | --- | --- |
| Example 1 | HPMCAS-1 | 76.7 |
| Example 2 | HPMCAS-2 | 72.2 |
| Example 3 | HPMCAS-3 | 70.0 |
| Example 4 | HPMCAS-4 | 68.9 |
| Comp. Ex. 1 | HPMCAS-7 | 48.0 |
| Comp. Ex. 2 | nifedipine bulk powder | 13.3 |

The powder obtained in each of Examples 1 to 4 showed marked improvement in dissolution rate of nifedipine compared with the nifedipine bulk powder in Comparative Example 2. The powder obtained in Comparative Example 1 was inferior in dissolution improvement to those obtained in Examples 1 to 4. This is presumably because solubility was insufficient during hot-melt extrusion and formation of a solid dispersion was insufficient owing to a large particle size and a high loose bulk density.

Powder X-ray diffraction analysis was carried out with respect to the powder obtained in each of Examples 1 to 4. Consequently, no crystal peak characteristic of nifedipine was observed. Thus, it is evident that in a solid dispersion obtained by hot-melt extrusion, nifedipine is dispersed in an amorphous form in the HPMCAS.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. Hypromellose acetate succinate for use as a hot-melt extrusion carrier having a volume-average particle size ($D_{50}$) as measured by dry laser diffraction of from 70 to 300 μm and a loose bulk density of from 0.25 to 0.40 g/cm$^3$, wherein the hypromellose acetate succinate has a degree of compaction of from 15 to 40 %.

2. A hot-melt extrusion composition comprising the hypromellose acetate succinate as claimed in claim 1 and a drug.

3. The hot-melt extrusion composition according to claim 2, wherein the drug is a poorly water-soluble drug.

4. A method for producing a hot-melt extrudate, comprising the steps of:
hot-melting a hot-melt extrusion composition comprising hypromellose acetate succinate having a volume-average particle size ($D_{50}$) as measured by dry laser diffraction of from 70 to 300 μm a loose bulk density of from 0.25 to 0.40 g/cm³, and a degree of compaction of from 15 to 40 %, and a drug at a hot-melt temperature equal to or higher than a melting temperature of the hypromellose acetate succinate, or at a hot-melt temperature equal to or higher than a temperature at which both of the hypromellose acetate succinate and the drug become melt to provide a hot-melted composition; and
extruding the hot-melted composition.

5. The method for producing a hot-melt extrudate according to claim 4, wherein the hot-melt temperature is from 50 to 250° C.

6. The hypromellose acetate succinate according to claim 1, wherein the degree of compaction is from 20.2 to 28.2%.

7. The hypromellose acetate succinate according to claim 1, wherein the hypromellose acetate succinate has an angle of repose from 30 to 45°.

8. The hypromellose acetate succinate according to claim 1, wherein the hypromellose acetate succinate has an angle of repose from 30 to 40°.

9. A composition comprising the hypromellose acetate succinate according to claim 1 and a plasticizer or a surfactant, wherein the composition is a hot-melt extrusion composition.

10. The hypromellose acetate succinate according to claim 1, wherein the degree of compaction is from 15 to 35%.

11. A hot-melt extrusion composition comprising the hypromellose acetate succinate as claimed in claim 10 and a drug.

12. The hot-melt extrusion composition according to claim 11, wherein the drug is a poorly water-soluble drug.

* * * * *

UNITED STATES PATENT AND TRADEMARK OFFICE
CERTIFICATE OF CORRECTION

PATENT NO. : 11,090,295 B2  Page 1 of 1
APPLICATION NO. : 14/453935
DATED : August 17, 2021
INVENTOR(S) : Maruyama et al.

It is certified that error appears in the above-identified patent and that said Letters Patent is hereby corrected as shown below:

On the Title Page

(57) Abstract, Line 3: Please correct "300 as" to read -- 300 µm as --

In the Claims

Column 13, Line 11, Claim 4: Please correct "300 µm a" to read -- 300 µm, a --

Signed and Sealed this
First Day of March, 2022

Drew Hirshfeld
*Performing the Functions and Duties of the*
*Under Secretary of Commerce for Intellectual Property and*
*Director of the United States Patent and Trademark Office*